United States Patent [19]

Smith

[11] Patent Number: 5,620,460

[45] Date of Patent: *Apr. 15, 1997

[54] SURGICAL NEEDLE HOLDER

[76] Inventor: James R. Smith, Flat 2, 193 Sutherland Avenue, Little Venice, London W9 1ET, England

[*] Notice: The term of this patent shall not extend beyond the expiration date of Pat. No. 5,487,749.

[21] Appl. No.: 493,604

[22] Filed: Jun. 22, 1995

Related U.S. Application Data

[63] Continuation of Ser. No. 216,398, Mar. 23, 1994, Pat. No. 5,487,749.

[30] Foreign Application Priority Data

Mar. 24, 1993 [GB] United Kingdom ............... 9306080

[51] Int. Cl.⁶ ...................................................... A61B 17/32
[52] U.S. Cl. ............................................................... 606/205
[58] Field of Search ................................ 606/205–209, 606/148

[56] References Cited

U.S. PATENT DOCUMENTS

| | | |
|---|---|---|
| 1,510,416 | 9/1924 | Pietz et al. . |
| 2,726,657 | 12/1955 | Tabrah . |
| 3,302,648 | 2/1967 | Nelson . |
| 3,404,683 | 10/1968 | Eizenberg . |
| 3,735,763 | 5/1973 | Shannon et al. . |
| 4,226,240 | 10/1980 | Walker, Jr. . |
| 4,226,241 | 10/1980 | Walker, Jr. . |
| 4,597,390 | 7/1986 | Mulhollan et al. . |
| 4,793,349 | 12/1988 | Weinrib . |
| 5,222,962 | 6/1993 | Burkhart . |
| 5,251,642 | 10/1993 | Handlos . |

FOREIGN PATENT DOCUMENTS

| | | |
|---|---|---|
| 628277 | 10/1961 | Canada . |
| 2420512 | 4/1975 | Germany . |
| 1362464 | 12/1987 | U.S.S.R. . |
| 1743593 | 6/1992 | U.S.S.R. . |
| 2210574 | 9/1988 | United Kingdom . |

OTHER PUBLICATIONS

Reducing the Risk of Infection for Obstetricians, British Journal of Obstetrics and Gynecology, Feb. 1991 vol. 98, pp. 124–126.

V. Mueller & Co., "A Comprehensive Guide to Purchasing", Chicago, Ill. pp. 460 and 171, 1956.

The Lawton Co., "Surgical Instrument Catalog", New York, pp. 24 and 25, 1957.

*Primary Examiner*—Michael Powell Buiz
*Assistant Examiner*—Nancy Connolly Mulcare
*Attorney, Agent, or Firm*—Lowe, Price, LeBlanc & Becker

[57] ABSTRACT

A surgical needle holder is provided for guarding the tip of a needle in an inoperative position. The needle tip is guarded in the inoperative position in retaining means such as a groove or slot associated with the jaws of the needle holder.

8 Claims, 2 Drawing Sheets

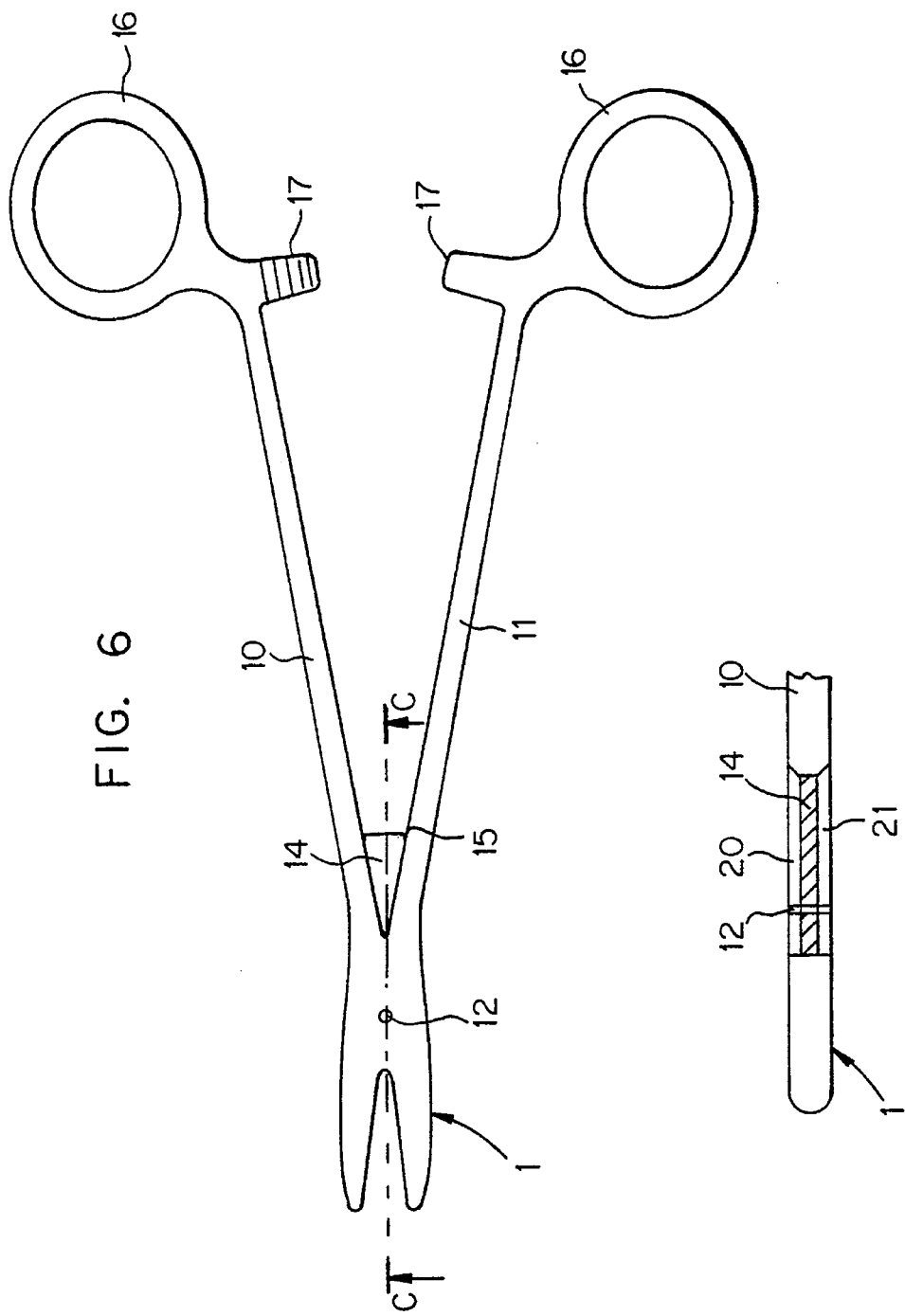

SURGICAL NEEDLE HOLDER

This application is a continuation of application Ser. No. 08/216,398 filed Mar. 23, 1994, now U.S. Pat. No. 5,487,719.

FIELD OF THE INVENTION

This invention relates to surgical instruments and in particular to a novel needle holder.

BACKGROUND ART

The increasing perception of risk of infection of medical personnel by contact with patients body fluids has led to various measures in an attempt to reduce the likelihood of infection. There is particular concern over the possibility of transmission of hepatitis B virus (HBV) and human immuno deficiency virus (HIV) to health workers in the course of their patient care duties. In the case of surgeons and other theatre workers, needle stick injuries are relatively common and surgical gloves do not provide complete protection. In one recent study it was found that in 54% of caesarean sections, one or more glove punctures were found to have occurred to the surgeon's gloves. Attempts have been made to reduce the puncture rate, for example, by adopting a practice of double-gloving and using blunt-tipped needles. While blunt tipped needles do reduce the number of punctures, perhaps by a factor of about 1.5, the rate of puncturing is still unacceptably high.

SUMMARY OF THE INVENTION

It is, therefore, an object of the invention to provide a needle holder which, in use, is capable of reducing the risk of needle stick injury and glove puncture in surgical operations.

According to one aspect of the present invention there is provided a surgical needle holder which comprises a pair of jaw or holding a needle, while inserting stitches into tissue and retaining means associated with the jaws for retaining the tip of the needle in an inoperative position, in which the user's hand is protected from contact with the needle tip.

The retaining means may comprise an aperture, recess or groove formed in part of the jaws of the instrument, the aperture, recess or groove being dimensioned to receive the needle tip. In an alternative arrangement, the jaws or the handles of the needle holder are shaped to provide abutments adapted to grip the needle tip or an elongated gap in which the needle tip can be lodged in the inoperative position.

The needle holder is preferably provided with the retaining means on opposite sides of the jaws so that the needle holder can be used either way up.

The needle holder in accordance with the invention is intended to be used with both blunt tipped and sharp needles and needles of various diameters. For this reason, the retaining means, such as a groove, when viewed in cross-section, has an inward taper.

BRIEF DESCRIPTION OF DRAWINGS

Further features and advantages of the invention will become apparent from the following description and accompanying drawings, in which:

FIG. 6 is a plan view of a fourth embodiment in accordance with the invention, and FIG. 7 is a view taken on the line C—C in FIG. 6.

DESCRIPTION OF PREFERRED EMBODIMENTS

Figure 1:
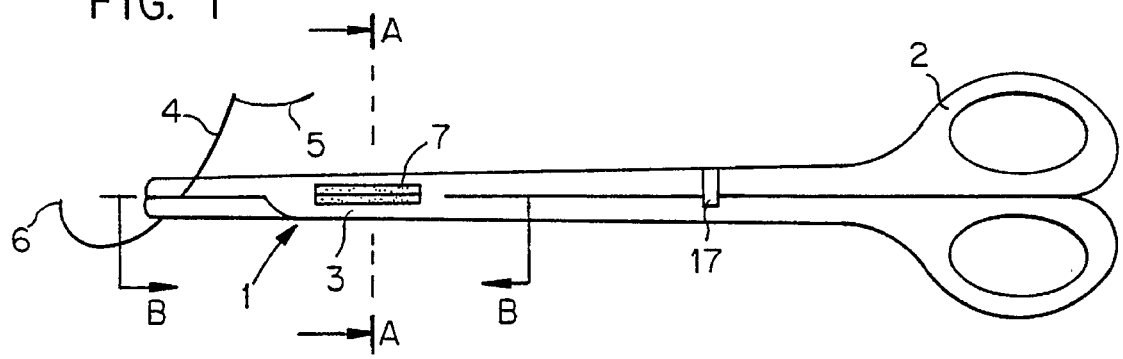
FIG. 1 is a perspective view of a needle holder in accordance with the invention, showing the needle in the operative position.

Referring the accompanying drawings, the needle holder comprises a pair of jaws generally indicated at 1, and which can be opened and shut using the handles 2. The action of the jaws is a scissor-like action pivoted in the general region of a pivot point 3. As shown in FIG. 1, a needle 4 is held in the jaws with thread 5 attached to the needle end and the needle tip 6 used to insert stitches in conventional manner to suture the wound. The needle holder normally incorporates a ratchet-type lock schematically indicated at 17.

Figure 3:
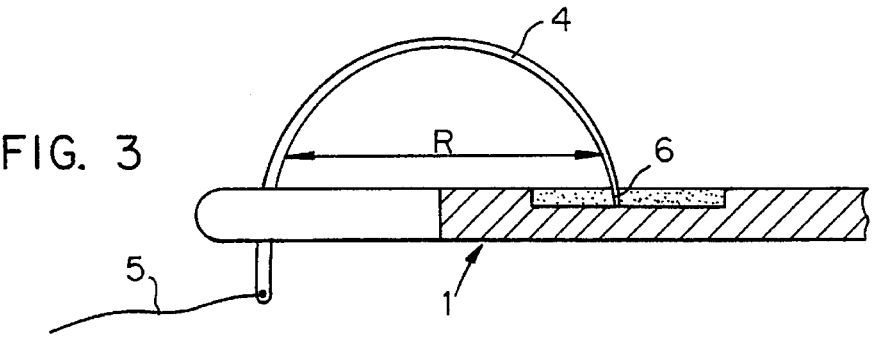
FIG. 3 is a view, partly in section taken along the line B—B in FIG. 1 and again on an enlarged scale.

After inserting stitches into the word it is common practice for a surgeon to leave the needle locked into the jaws and to slide his hands down the instrument to grip the surgical thread and firmly close up the wound. It is at this point that it is believed that a number of glove punctures and needle stick injuries occur. In accordance with the invention, at this point in the suturing of the wound, the needle 4 is rotated in the jaws so that the needle tip 6 is received in a groove 7, in which it is releasably retained. In this position (which is indicated in FIG. 3), the needle tip 6 is guarded within the groove and the surgeon is protected from any needle stick injury. He can therefore complete the tying of the surgical suture without risk of glove puncture. Also, when the surgeon passes the needle and needle holder to the theatre nurse, the needle should be passed in the inoperative position.

Figure 2:
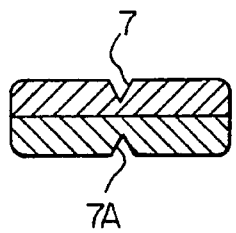
FIG. 2 is a section along the line A—A in FIG. 1, on an enlarged scale.

The groove 7 is formed in one or both components of the jaw 1 and in one embodiment is shaped as shown in FIG. 2, at an inwardly tapering groove. The advantage of this kind of shape is that the groove can accommodate needles of various tip sizes. The length of the groove 7 is also chosen so that it can accommodate a variety of needles of different diameter R (see FIG. 3). It may also be advantageous to provide the inner surface of the groove 7 with a milled or toughened surface for better retention of the needle tips. An inwardly tapering groove can also be used with blunt-tip needles and these are advantageously used together with the needle holder of the invention, so as to further reduce the risk of needle stick injury.

Rotation of the needle from the operative to the inoperative or parked position shown in FIG. 3 is preferably carried out using forceps to rotate the needle into the parked position. Suitable forceps for this purpose are described in UK Patent Application No. 2210574, the contents of which are hereby incorporated by reference.

Figure 4:
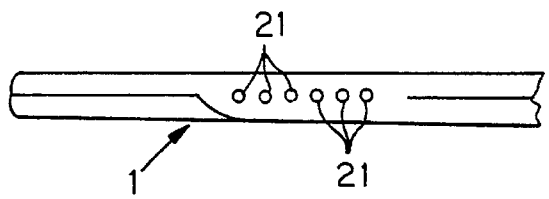
FIG. 4 shows a plane view of the jaws section of a second embodiment of a needle holder in accordance with the invention.

A second embodiment of the invention is shown in FIG. 4. This embodiment corresponds with that shown in FIGS.

1 to 3 except that instead of a groove, one or both jaws 1 are formed with a series of holes, recesses or depressions 21. Such holes, recesses or depressions may also be inwardly tapered so as to accommodate needle tips of different sizes. Preferably, the holes or recesses 21 are formed on the face of both jaws 21 so that the needle tip call be received in an appropriate hole whichever way up the needle holder is used.

Figure 5:
FIG. 5 shows a plan view of the jaws section of a third embodiment of a needle holder in accordance with the invention.

A third embodiment is shown in FIG. 5. In this embodiment, instead of providing a groove in the jaws 1, the proximal end of the jaws are modified to form a slot 31. This slot may be tapered inwardly to accommodate needle tips of different sizes.

Referring to FIGS. 6 and 7, a fourth embodiment comprises a needle holder having jaws formed by a pair of handles 10,11 pivotably attached at a pivot point 12. Handle 10 includes a web-like plate 14 attached to the handle 10. Flats 14 extends into a slot formed in the handle 11 and the two handles are pivoted about a pin 12. Plate 14 has an extension in the direction of the finger grips 16. Handle 10 and 11 are so shaped in the region of the rearward plate extension 15 that when the needle holder is closed, an enlarged gap 20 or 21 exists between the arms of the handles. A ratchet closure 17 enables the needle holder to be held in a closed position without maintaining finger pressure on the handles. The inward faces of the portions of the arms 10 and 11 which form the sides of the gap 20 or 21 may be sloped inwardly so as to form inwardly tapered slots in cross-section.

In a magnification of the embodiments shown in FIG. 5 or FIGS. 6 and 7, additional retaining means (e.g. a groove or recesses) may be formed in one or both faces of the jaws in the region of the pivot point. This arrangement allows needles to be accommodated which have a larger range of diameters.

Preferably, the retaining means comprise a groove or slot having a substantially uniform width. In comparison with a standard needle holder, it may be desirable to shift the pivot point forward (i.e. in the direction of the open end of the jaws), in order to provide the maximum length of available area for locating the groove and/or slot. Also, in order to be able to provide retaining means of significant width and depth, the bulk size of the needle holder in the region of the jaws may need to be increased compared with some standard or conventional needle holders.

In a more elaborate design, the needle holder may be modified by the provision on a rolling hinge. In such a modification, movement of one handle axially with respect to the other causes the needle to rotate from its operative to its inoperative position, without needing to touch the needle with forceps. Once the needle is in its inoperative position, the tip may then be urged into a retaining means such as a groove.

What I claim is:

1. A surgical needle holder which comprises:
    a) a pair of elongate members which are linked together at a pivot point in scissors-like fashion and which include projecting jaw portions forming jaws for releasably holding a surgical needle; and
    a pair of handle portions for opening and closing the jaws, each said handle portion comprising an elongated portion extending between a handle portion grip and said pivot point, said elongated portion widening into an enlarged portion containing said pivot point, each said handle portion including an outer and an inner side, inner sides of said pair of handle portions facing each other, wherein one of said handle portions further comprising means for retaining a tip of the surgical needle in a position wherein the needle tip is contained so as to be inoperative when the projecting jaw portions are closed, said retaining means provided in an outer side of at least one of said pair of handle portions and including a surface depression in said enlarged portion of said handle portion, said surface depression containing said surgical needle so as to be inoperative.

2. The surgical needle holder of claim 1 wherein said means for retaining further comprises a recess or groove in said outer side of said at least one of said enlarged portions.

3. A needle holder according to claim 2 wherein said recess or groove form an opening having sidewalls which are uniformly spaced apart.

4. A needle holder as claimed in claim 1, wherein said retaining means is provided in said enlarged portions of both handle portions whereby the needle holder can be used either way up.

5. A needle holder as claimed in claim 1 which comprises a pair of handles linked together at a pivot point, said pivot point including a rolling hinge whereby movement of one handle axially with respect to the other causes the needle to rotate from its operative to its inoperative position.

6. A surgical needle holder which comprises:
    a) a pair of elongate members which are linked together at a pivot point in scissors-like fashion and which include projecting jaw portions forming jaws for releasable holding a surgical needle;
    b) handle portions for opening and closing the jaws, said handle portions being shaped to provide a gap between the handle portions in the region of the pivot point when the projecting jaw portions are closed, said gap being dimensioned to receive a tip of the surgical needle; and
    c) wherein one of said handle portions includes a protrusion extending therefrom and towards the other handle portion, said protrusion being located on said at least one handle portion to extend into said gap so as to guard the tip of the needle and prevent the needle tip passing between the handle portions and wherein said other handle portion includes a slot into which said protrusion extends when said jaw portion hold said surgical needle.

7. A needle holder as claimed in claim 6, wherein said handle portions are pivoted to move in a major plane and wherein said protrusion comprises a plate which extends from an inner face of said one handle portion at a point in its depth such as to provide, when the jaws are closed, open channels for receiving the needle tip, said which channels opening in both directions at right angles to a major plane of the needle holder.

8. A needle holder as claimed in claim 6 wherein said handle portions comprises an inner side and an outer side and wherein at least one of said handle portions is formed in said outer side with retaining means for retaining a tip of a surgical needle.

* * * * *